US010561792B2

(12) United States Patent
Holtwick et al.

(10) Patent No.: US 10,561,792 B2
(45) Date of Patent: Feb. 18, 2020

(54) DRUG DELIVERY DEVICE FOR THE DELIVERY OF TWO MEDICAMENTS

(71) Applicant: Sanofi-Aventis Deutschland GMBH, Frankfurt am Main (DE)

(72) Inventors: Marc Holtwick, Frankfurt am Main (DE); Wolfgang Marx, Frankfurt am Main (DE); Andreas Bode, Frankfurt am Main (DE); James West, Crescent Bristol (GB); Paul Hayton, Bristol (GB); James Coop, Bristol (GB); Christopher Kilbane, Bristol (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 625 days.

(21) Appl. No.: 15/309,764

(22) PCT Filed: May 27, 2015

(86) PCT No.: PCT/EP2015/061628
§ 371 (c)(1),
(2) Date: Nov. 8, 2016

(87) PCT Pub. No.: WO2015/181192
PCT Pub. Date: Dec. 3, 2015

(65) Prior Publication Data
US 2017/0151389 A1    Jun. 1, 2017

(30) Foreign Application Priority Data
May 28, 2014    (EP) .................................... 14170339

(51) Int. Cl.
*A61M 5/24*    (2006.01)
*A61M 5/20*    (2006.01)
(Continued)

(52) U.S. Cl.
CPC ............ *A61M 5/2448* (2013.01); *A61M 5/19* (2013.01); *A61M 5/2066* (2013.01);
(Continued)

(58) Field of Classification Search
CPC .... A61M 5/2448; A61M 5/2066; A61M 5/19; A61M 5/3155; A61M 5/3158
See application file for complete search history.

(56) References Cited

U.S. PATENT DOCUMENTS 5,253,785 A * 10/1993 Haber ..................... A61M 5/19
222/135
5,505,704 A * 4/1996 Pawelka ................. A61M 5/19
604/191
(Continued)

FOREIGN PATENT DOCUMENTS

DE    19930631    1/2001
GB    2497375    6/2013
(Continued)

OTHER PUBLICATIONS

International Preliminary Report on Patentability in International Application No. PCT/EP2015/061628, dated Nov. 29, 2016, 10 pages.
(Continued)

*Primary Examiner* — Andrew M Gilbert
(74) *Attorney, Agent, or Firm* — Fish & Richardson P.C.

(57) ABSTRACT

The disclosure is directed to a drug delivery device comprising a housing retaining a primary drug delivery assembly and a secondary drug delivery assembly. The secondary drug delivery assembly comprises a secondary dose setting mechanism with a biasing member adapted to reset the secondary dose setting mechanism in a resetting movement. An actuator is movable relative to the housing and comprises a first engagement section configured to engage a (Continued)

second engagement section provided by an actuation collar such that an actuation movement of the actuator is transferred to the actuation collar. A setting element is movable between a first position and a second position and is connected to the secondary dose setting mechanism such that during the resetting movement of the secondary dose setting mechanism, the setting element is moved from the second position into the first position.

20 Claims, 8 Drawing Sheets

(51) Int. Cl.
  *A61M 5/315* (2006.01)
  *A61M 5/19* (2006.01)
(52) U.S. Cl.
  CPC ........ *A61M 5/3155* (2013.01); *A61M 5/3158* (2013.01); *A61M 5/2455* (2013.01)

(56) References Cited

U.S. PATENT DOCUMENTS

| | | | | |
|---|---|---|---|---|
| 9,248,239 | B2* | 2/2016 | Leak | A61M 5/3155 |
| 9,333,303 | B2* | 5/2016 | Leak | A61M 5/19 |
| 2004/0011816 | A1* | 1/2004 | Muhlbauer | A61C 9/0026 |
| | | | | 222/137 |
| 2007/0060894 | A1* | 3/2007 | Dai | A61M 5/19 |
| | | | | 604/207 |
| 2010/0143864 | A1* | 6/2010 | An | A61C 9/0026 |
| | | | | 433/89 |
| 2012/0148980 | A1* | 6/2012 | Gramann | A61C 5/64 |
| | | | | 433/90 |
| 2013/0197447 | A1* | 8/2013 | Smith | A61M 5/19 |
| | | | | 604/191 |
| 2013/0253440 | A1* | 9/2013 | Smith | A61M 5/31565 |
| | | | | 604/246 |
| 2013/0261556 | A1* | 10/2013 | Jones | A61M 5/19 |
| | | | | 604/191 |
| 2014/0005603 | A1* | 1/2014 | Holtwick | A61M 5/19 |
| | | | | 604/110 |
| 2017/0165430 | A1* | 6/2017 | Holtwick | A61M 5/19 |

FOREIGN PATENT DOCUMENTS

| | | |
|---|---|---|
| JP | 2013-539695 | 10/2013 |
| WO | WO 2011/101351 | 8/2011 |
| WO | WO 2011/117404 | 9/2011 |
| WO | WO 2012/049139 | 4/2012 |
| WO | WO 2012/072539 | 6/2012 |
| WO | WO 2012/072569 | 6/2012 |

OTHER PUBLICATIONS

International Search Report and Written Opinion in International Application No. PCT/EP2015/061628, dated Aug. 12, 2015, 13 pages.

* cited by examiner

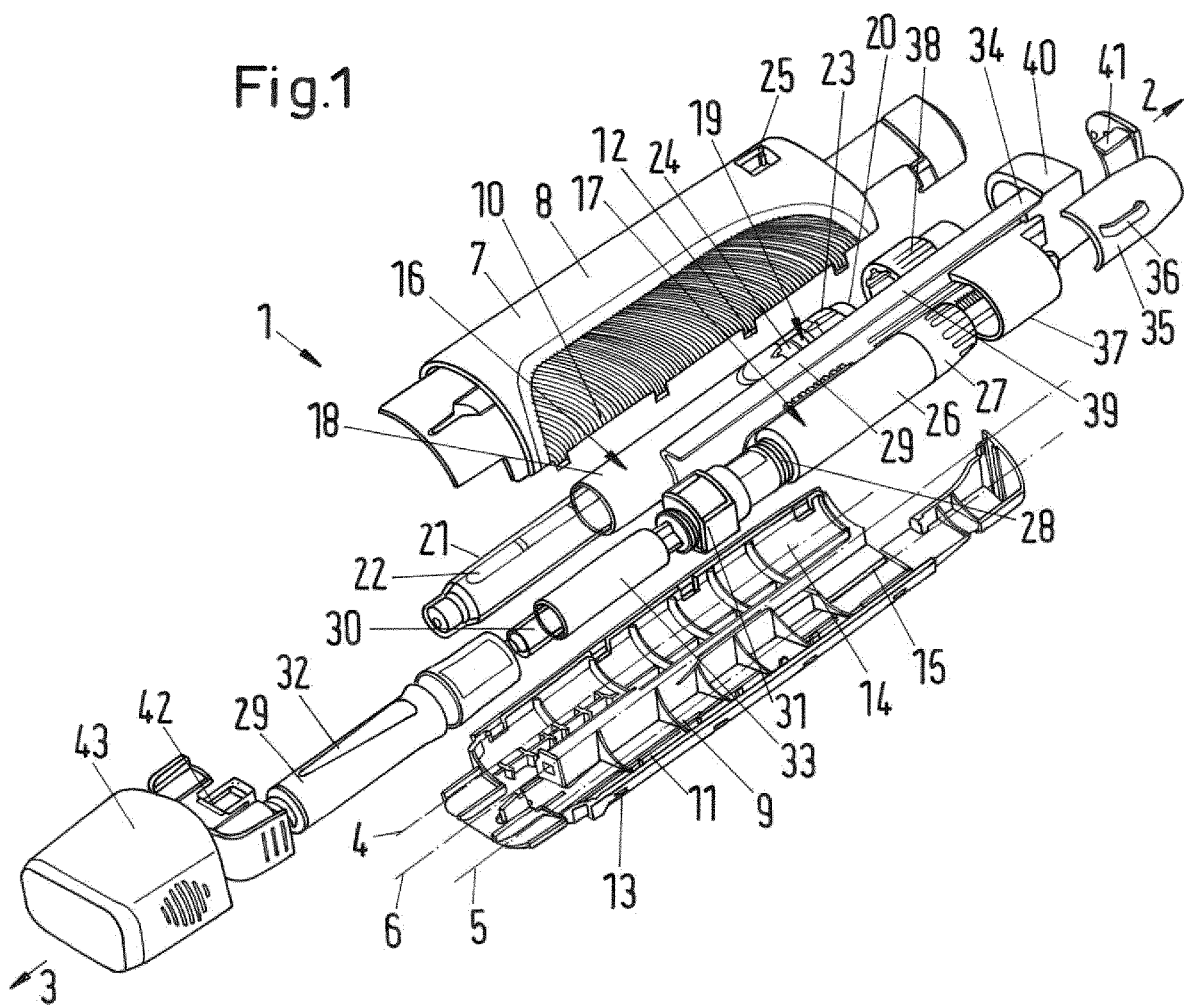

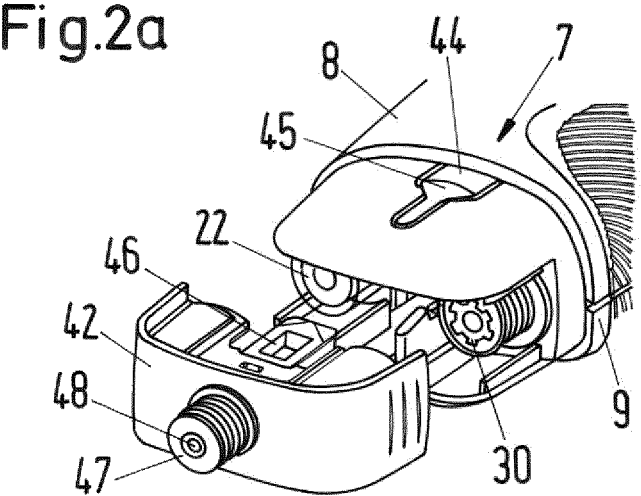
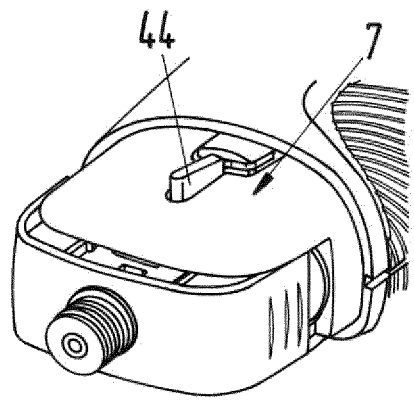
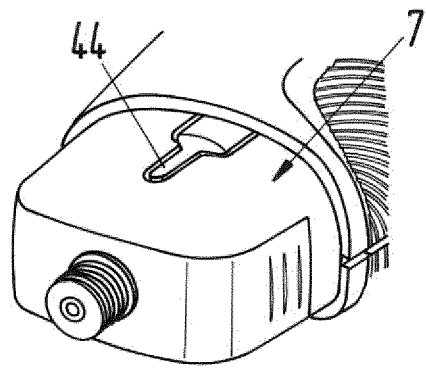

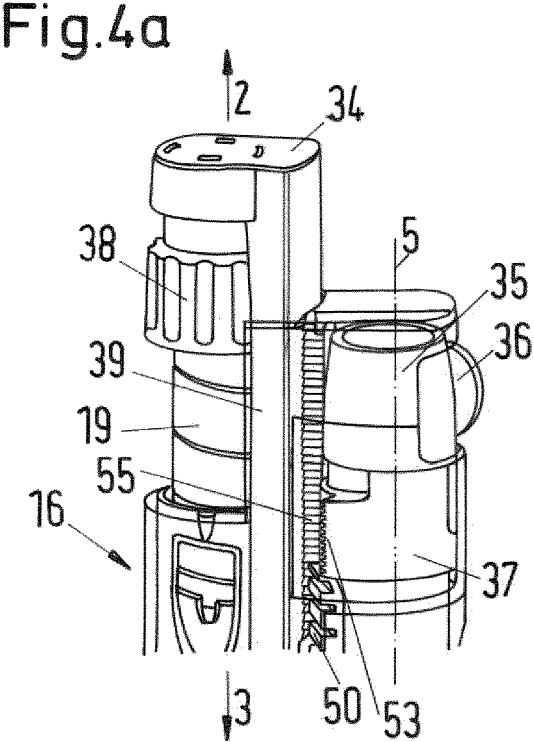
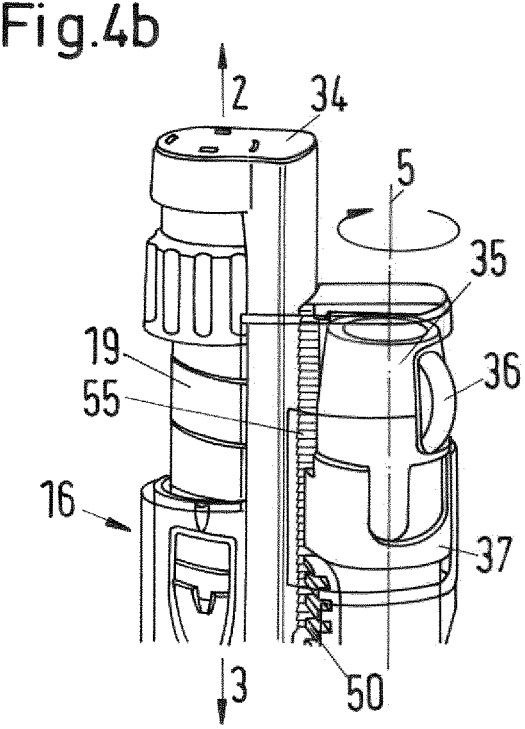
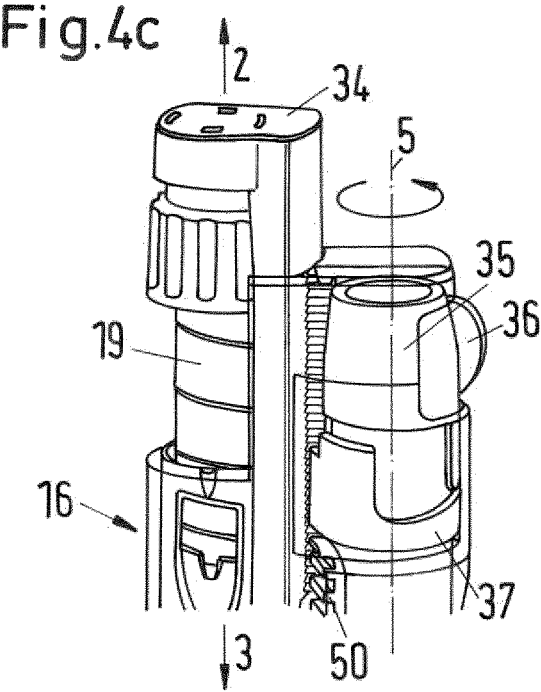
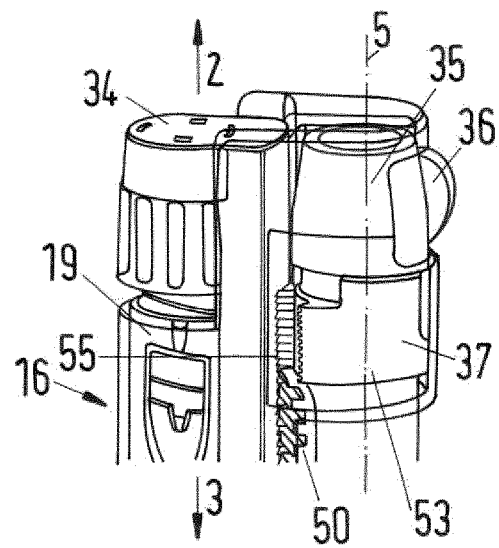

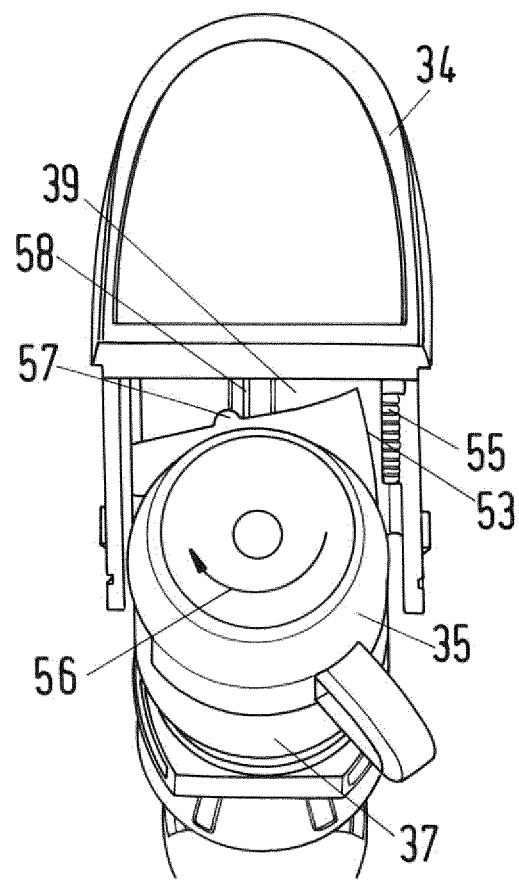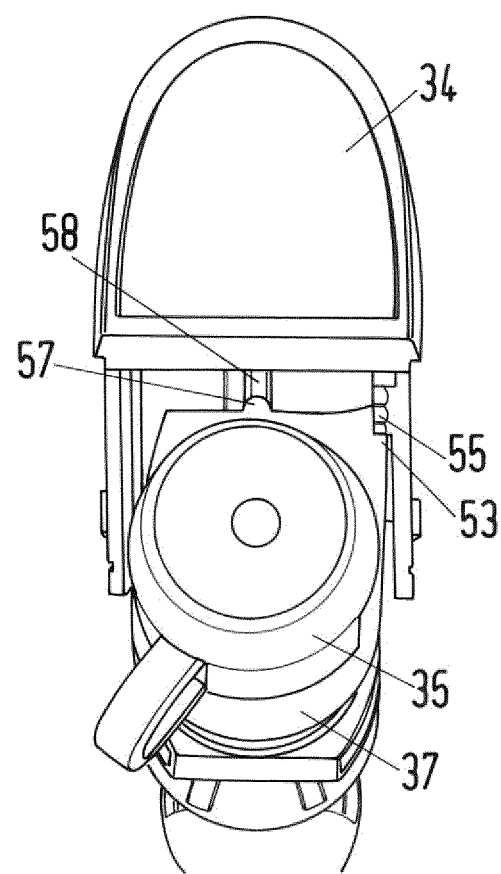

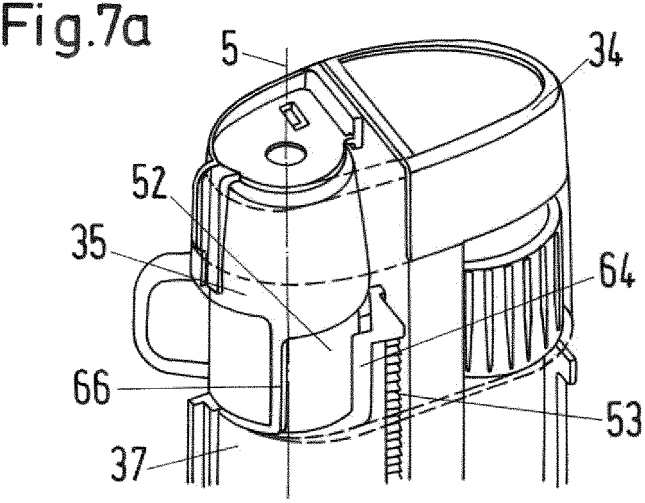
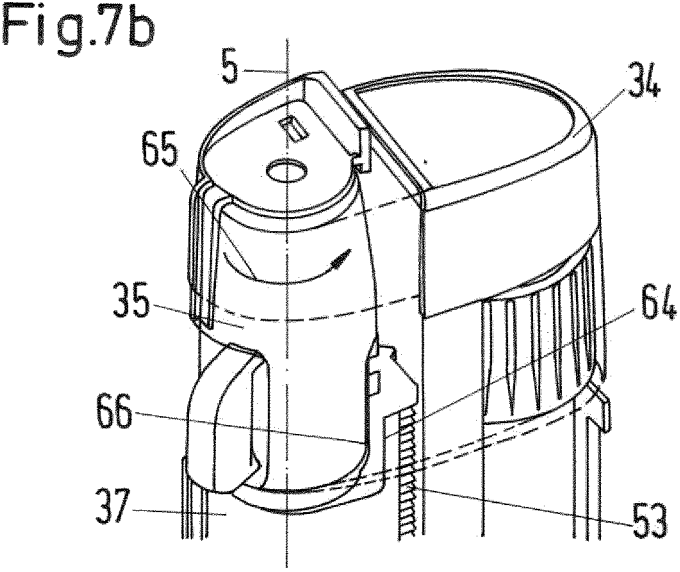
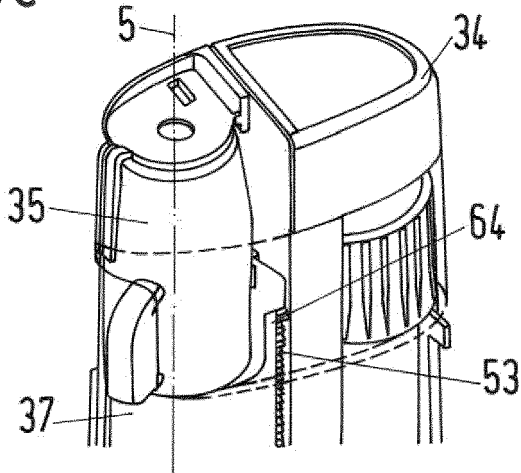

DRUG DELIVERY DEVICE FOR THE DELIVERY OF TWO MEDICAMENTS

CROSS-REFERENCE TO RELATED APPLICATIONS

This application is a U.S. national stage application under 35 USC § 371 of International Application No PCT/EP2015/061628, filed on May 27, 2015, which claims priority to European Patent Application No. 14170339.7 filed on May 28, 2014, the entire contents of which are incorporated herein by reference.

The disclosure is directed to a drug delivery device comprising a housing which retains two drug delivery assemblies.

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. Another example of a medicament combination is the administration of a pain reliever in combination with a medicament for treating osteoarthritis.

Drug delivery devices of the aforementioned kind often have applications where regular injection by persons without former medical training occurs. This is increasingly common among patients having diabetes or the like, e.g. osteoarthritis. Self-treatment enables such patients to conduct effective management of their disease.

In combination therapy, a primary medicament and a secondary medicament are delivered in a specific relationship to deliver the optimum therapeutic dose. The injection devices of the generic kind usually comprise a housing in which two or more drug delivery assemblies are retained. Such devices include a primary drug delivery assembly for dispensing the primary medicament such as long-acting insulin and a secondary drug delivery assembly for dispensing the secondary medicament, such as GLP-1. Some kinds of drug delivery assemblies comprise a compartment such as a cartridge holder for accommodating a replaceable medicament container such as a cartridge which stores the medicament.

In some cases, depending on the patient or the stage of the therapy, an effective treatment requires variations in the quantities and/or proportions of the medicaments making up the combined therapy. For example, the patient may require a non-adjustable fixed dose of e.g. the secondary medicament in combination with an adjustable variable dose of the primary medicament.

WO 2012/072569 A1 discloses a drug delivery device with a housing retaining a first drug delivery device and a second drug delivery device. The drug delivery devices comprise a dose setting mechanism, each. A dose limiting system mechanically couples the dose setting mechanisms. The first dose setting mechanism includes a drive gear which is coupled a dose dial such that by rotating the dose dial, the drive gear in rotated in the same direction. The second dose setting mechanism includes a driven gear which constantly engages the drive gear and which engages a spindle by an internal thread.

WO 2012/072539 A1 discloses a drug delivery device and a method for sequentially delivering at least two medicaments. The device includes a rotationally driven variable dose setting mechanism operably connected to a first cartridge containing a first medicament and a fixed dose setting mechanism operably connected to a second cartridge containing a second medicament. A splined dose setter is connected to both setting mechanism.

The effectiveness of a combined delivery of medicaments may require one or more doses to be delivered sequentially with one of the two medicaments being injected into the human body prior to the delivery of the other medicament. Such treatment may be conducted with devices that include two separate dispensing mechanisms that are actuated independently from each other such that the dispensing mechanisms are activated successively. This, however, may be hazardous for patients that are physically or mentally impaired or otherwise disadvantaged. It is desirable to have a device that is provided with merely one dispense button, respectively an actuator, which the patient can trigger and which leads to a sequential delivery of the primary and the secondary medicament. Known in the art are also electrical drug delivery devices, but these devices require an electrical energy source and are rather expensive and complex in their design.

New developed drug delivery devices also have to pass long-time approval procedure before competent authorities before they can be placed on the market, as setting mechanisms and the like have to fulfill strict requirements. In this regard, it would be favorable, especially for manufactures, to be able to fall back on that have already been approved. Facing these challenges, there is a strong need for devices and device components for the delivery of two or more medicaments that are suitable for injecting different medication profiles in a single injection or delivery step. The setting of the doses and the injection procedure should be safe, simple, manageable and convenient for the user to perform. Furthermore, it is important that after the medicaments have been injected, the device needs to be set back to an initial state so that the device is ready for a further administration such that the user can start over to set doses of the two medicaments, e.g. from 0 units to the required value, and to start the injection of the combined medication.

Some aspects of the disclosure can be implemented to provide a drug delivery device with improved user handling and/or improved safety properties. For example, to provide for a drug delivery device with an improved setting process in which doses of multiple medicaments are set. Setting a medicament dose in one drug delivery assembly could be free from improper influences from the other drug delivery assembly.

The above problem is solved by a drug delivery device as defined in claim 1 and a drug delivery device as defined in claim 15.

A drug delivery device is provided which comprises a housing, the housing retaining a primary drug delivery assembly and a secondary drug delivery assembly, wherein the secondary drug delivery assembly comprises a secondary dose setting mechanism.

In particular, the secondary dose setting mechanism comprises a biasing member adapted to reset the secondary dose setting mechanism in a resetting movement. An actuator is arranged such that it is movable relative to the housing, preferably along a first longitudinal axis of the housing, wherein the actuator comprises a first engagement section configured to engage a second engagement section provided by an actuation collar such that an actuation movement of the actuator is transferred to the actuation collar. A preferably lever actuatable setting element is movable between a first position and a second position. The setting element is connected to the secondary dose setting mechanism such that during the resetting movement of the secondary dose setting mechanism, the setting element is moved from the second position into the first position, wherein the setting element is configured to drive the actuation collar out of engagement with the actuator, resp. to disengage the actuation collar from the actuator when being moved from the second position into the first position. When the setting element is in the first position, the actuation collar is disengaged from the actuator. When the setting element is in the second position, the actuation collar engages the actuator such that the actuation movement can be transferred. The secondary drug delivery assembly may be configured to receive a secondary reservoir containing a secondary medicament.

Some aspects of the disclosure can be implemented to provide a drug delivery device in which the secondary dose setting mechanism can be effectively operated by the user without influences from the primary dose setting mechanism. Since the resetting movement comes along with the disengagement between actuation collar and actuator, the drug delivery device has improved operating safety properties.

The first and the second longitudinal axis may be aligned in a parallel relationship and preferably parallel to a longitudinal axis of the housing. First longitudinal axis or second longitudinal axis may also coincide with the longitudinal axis of the housing. Moreover, the first and the second longitudinal axis may extend from a proximal end of the housing to a distal end of the housing. The distal end of the housing may correspond to a dispensing end, such that actuation of a first and/or a second dispensing mechanism of the first and/or the second drug delivery assembly retained in a respective receiving section of the housing causes the respective medicament to flow in distal direction. Accordingly, the distal end may be configured for attachment to a dispense interface, which may comprise an injection needle. An axis between the distal end and the proximal end of the housing may correspond to or may be parallel to the longitudinal axis of the housing. The proximal end of the housing may correspond to an actuation end, where the user may actuate the actuator, preferably by driving the actuator in distal direction. The first position of the setting element may correspond to an initial position of the setting element prior to setting a medicament dose. The second position may correspond to a final position of the setting element after the setting process, respectively after the medicament dose has been set.

The actuator may be movable relative to the housing between a first, e.g. proximal, and a second, e.g. distal, position and may also be arranged such that it is movable along the first longitudinal axis of the housing. The actuator may be slidably received in the housing. The housing may be provided with guiding means such as inner webs formed on inner surfaces of the housing and configured to guide the actuator during the actuation movement. During the actuation movement, which may correspond to a longitudinal displacement of the actuator in a distal direction parallel to the first and/or the second longitudinal axis, the user may move the actuator towards the distal end of the housing.

The setting element may be movable relative to the housing. The setting element may be movable around a second longitudinal axis between the first position and the second position during setting movement. The actuatable setting element may be configured such that it can be manipulated from the outside of the housing by the user. The actuation collar may be movable between a non-engagement position relative to the actuator where the first engagement section and the second engagement section are not engaged and an engagement position relative to the actuator where the first engagement section and the second engagement section are engaged. In the first position of the setting element, the actuation collar is in the non-engagement position relative to the actuator and the actuator is free to move relative to the actuation collar. In the second position of the setting element, the actuation collar is in the engagement position with the actuator and engages the actuator such that an actuation movement of the actuator is transferred to the actuation collar. Accordingly, when the actuator is actuated by the user and moved from its first position to its second position, the actuation movement is transferred to the actuation collar such that the actuation collar is moved from a first position to a second position, e.g. from a first proximal position to a second distal position.

The setting movement may come along with the setting element driving the actuation collar into engagement with the actuator, wherein in the first position of the setting element, the actuator is free to move relative to the actuation collar and in the second position of the setting element, the actuation collar engages the actuator such that an actuation movement of the actuator is transferred to the actuation collar. The setting element may be adapted to the actuation collar such that the setting element moves the actuation collar from the non-engagement position with the actuator into the engagement position with the actuator when the setting element moves from the first position into the second position. For example, the setting element and the actuation collar may be provided with respective force transfer means such as abutment surfaces.

The setting movement of the setting element from the first into the second position may correspond to a predetermined or fixed set dose. The setting movement of the setting element from the first into the second position is transferred to the secondary dose setting mechanism such that a certain dose is set. Preferably, the size of the dose of the secondary medicament that is set with the setting movement is defined by the length of the setting movement between the first and the second position. The length of the setting movement may be predefined, resp. limited such that the set dose of the secondary medicament is a fixed resp. non-variable dose. For example, the first position may correspond to a set dose of zero units, which is the usual initial position before a dose is set by the patient. The second position may correspond to a set dose of e.g. 10 units. The actuation movement may take place after the setting process and may correspond to the action a patient conducts to inject the set dose of medicament. Such actuation movement is, for example, the displacement or the pressing of a dispense button.

The setting movement is preferably manually conducted by the user by operating the secondary dose setting mechanism of the secondary drug delivery assembly such as rotating a dose knob via the setting element and corresponds to the movement of the setting element from the first into the second position. Accordingly, the setting element may be rotated relative to a longitudinal axis of the secondary drug delivery assembly from the first position into the second position.

The resetting movement may be characterized as a reversed setting movement, in which the setting element is moved from the second position (e.g. 10 units) back into the first position (0 units). Another medicament dose may then be set.

The setting element is moved from the second position under the force of the relaxing biasing member. The resetting movement may happen during dispense. During dispense of a medicament in the secondary drug delivery assembly, the setting element is moved from the second position into the first position in the resetting movement because the setting element is coupled to the secondary dose setting mechanism such that the resetting movement of the secondary dose setting movement is transferred to the setting element. After dispense of the medicament, the setting element is in the first position and may be moved from the first into the second position to set a dose of the medicament in the secondary drug delivery assembly again.

The term "fixed dose" as used herein can be characterized as a dose value that is defined by the construction of the housing, the drug delivery assembly or the drug delivery device, wherein the user is only able to inject a specific dose. The user is not in the position to inject lower or higher doses of the medicament. The dose the user may effectively set and inject is restricted to a certain value.

On the contrary, the term "variable dose" can be characterized as a dose where the user is substantially free to choose the amount of medicament he wants to inject. The dose is variably adjustable, normally between upper and lower limits.

The biasing member may be connected the dose setting member such that the biasing member is prestressed when the dose setting element is moved from the first into the second position. The biasing member is stressed when the setting element is in the second position. The biasing member may be connected to the setting element such that the biasing member moves the setting element from the second into the first position when the biasing member relaxes. The biasing member is relaxed when the setting element is in the first position. For example, a dose setter such as a dose knob may be rotatably coupled to the secondary assembly housing such that rotation of the knob relative to the secondary assembly housing in a first direction results in prestressing or twisting of the biasing member. Preferably, the dose knob is rotated about a rotational axis parallel to the first longitudinal axis.

The secondary drug delivery assembly may comprise a secondary dose dispensing mechanism. The biasing member of the secondary dose setting mechanism, e.g. a spring, may be connected to the secondary dose dispensing mechanism such that the biasing member provides a dispensing force when the biasing member relaxes. During the setting movement, the biasing member is prestressed, which may not only build up the mechanical energy for the resetting movement but which may also build up the mechanical energy for the dispensing mechanism. By transforming the biasing member from the relaxed into the prestressed state, the mechanical energy is build up and stored until the biasing member is released so that the stored mechanical energy moves the setting element from the second position into the first position. At the same time, the mechanical energy may be used for the secondary dose dispensing mechanism.

A trigger button, a release button, dispense button or the like may be provided for releasing the prestressed biasing member (spring). By releasing the spring, the spring drives a drive member of the dose dispensing mechanism in axial direction, respectively distal direction relative to the housing of the secondary drug delivery assembly. Displacement of the drive member may force a bung or the like in a secondary reservoir of the secondary drug delivery assembly in distal direction such that a secondary medicament in the secondary reservoir is driven out of the secondary reservoir. The release of the biasing member force resets the setting element in the resetting movement, in which the setting movement of the setting element is reversed and the setting element is moved from the second position back into the first position. Such devices are also known as power assisted injectors, which can be characterized by an energy source such as stored mechanical energy provided by a prestressable spring to drive a medicament out of a cartridge.

Preferably, the actuator is part of the housing and may be configured such that a part or section of the actuator, e.g. an actuation button, is located outside the housing, while the first engagement section is located inside the housing. The mechanical connection between the actuator and the secondary dose setting mechanism is automatically disconnected after the secondary medicament is dispensed by moving the setting element from the second into the first position under the force of the biasing member. Dispense of the secondary medicament may be induced by the force of the biasing member of secondary dose setting mechanism. After the resetting of the setting element, the secondary dose setting mechanism is again free from mechanical influences by the actuator. In fact the housing does not affect the secondary dose setting mechanism. Accordingly, the secondary drug delivery assembly may be a commercially available drug delivery device such as a power assisted injector which is mounted within the housing. Thus, an approval procedure is not necessary.

Furthermore some aspects of the disclosure can be implemented to provide a drug delivery device with improved dispensing properties. By means of the single actuator of the drug delivery device, a primary dose dispensing mechanism of the primary drug delivery assembly and a secondary dose dispensing mechanism of the secondary drug delivery assembly can be effectively operated together. The primary drug delivery assembly may be configured to receive a primary reservoir containing a primary medicament.

Preferably, the primary drug delivery assembly is retained in a first receiving section of the housing and the secondary drug delivery assembly is retained in a second receiving section of the housing. The first longitudinal axis may extend through the first receiving section from a proximal end of the housing to a distal end of the housing. The second longitudinal axial may run through the second engagement section parallel to the first longitudinal axis. The actuator may be rotationally constrained with respect to the housing to ensure a rigid engagement between the first and the second engagement section. The actuator may comprise an actuating surface extending at least partially over the first receiving section in axial direction.

According to a further embodiment, the second drug delivery assembly comprises a secondary dose dispensing mechanism and the setting element is movable, preferably in a rotational movement about a second longitudinal axis, from the first position into the second position during a setting movement. The biasing member is connected to the setting element such that it is prestressed during the setting movement and released by activation of the secondary dose dispensing mechanism. The biasing member is caused to relax and drives the setting element from the second position into the first position. A preferably fixed dose of a secondary medicament in the secondary drug delivery assembly is set with the setting movement. The setting movement is manually conducted by the user by operating the secondary dose setting mechanism to set a dose of the secondary medicament with the setting element. The secondary dose setting mechanism is configured to allow the setting element to be in a stable position either in the first or in the second position. Accordingly, the dose setting mechanism may comprise a holding or locking mechanism configured to prevent the biasing member from relaxing when the setting element has been moved from the first towards the second position.

The actuation collar may at least partially surround the secondary drug delivery assembly in a sleeve-like manner. The actuation collar may be arranged with respect to the secondary dose dispensing mechanism, which may comprise a trigger button, such that a secondary dose dispensing mechanism is actuated when the actuation movement is transferred to the actuation collar. Preferably, the trigger button is movable from a first position into a second position. When the trigger button moves towards the second position, the trigger button releases the biasing member to initiate the resetting movement. Preferably, the actuation movement is transferred to the actuation collar such that the actuation collar moves the trigger button into the second position. By releasing the spring, the spring pushes a drive member of the secondary dose dispensing mechanism in distal direction relative to the housing of the secondary drug delivery assembly. By release of a spring force, the secondary dose setting mechanism is rotationally reset in the resetting movement in which the setting movement of the setting element is reversed and the setting element is moved back from the second position into the first position.

According to a further embodiment, the setting element and the actuation collar are disposed coaxially, wherein the setting element is rotatable relative to the actuation collar between a first relative rotational position and a second relative rotational position, wherein during the resetting movement, the setting element is moved from the first relative rotational position into the second relative rotational position such that the setting element rotationally engages the actuation collar. Thereby it is ensured, that the entire dose of the secondary medicament is dispensed before the first engagement section and the second engagement section are disengaged. In the first relative rotational position, the setting element is not engaged with the actuation collar such that the setting element moves relative to the actuation collar during the resetting movement. In the second relative rotational position, the setting element engages the actuation collar such that the movement of the setting element toward its first position is transferred to the actuation collar.

In one embodiment, the primary drug delivery assembly may comprise a primary dose setting mechanism and may be configured to receive a primary reservoir containing a primary medicament, wherein the primary dose setting mechanism and the secondary dose setting mechanism are configured to be set individually. In other words, the primary drug delivery assembly and the secondary drug delivery assembly do not share a common dose setter. Instead the user may operate the primary dose setting mechanism so that the dose of the primary medicament is set and the secondary dose setting mechanism so that the dose of the secondary medicament is set.

Each of the primary reservoir and the secondary reservoir may be a replaceable medicament container such as a cartridge containing a medicament.

In a further embodiment, the actuator engages the primary dose dispensing mechanism of the primary drug delivery assembly during an actuation movement such that a set dose of the primary medicament is dispensed through a dispense interface. Preferably, the primary dose setting mechanism may be operated independently from the secondary dose setting mechanism. Setting the dose of one of the medicaments does not influence or set a dose of the other medicament. The primary dose dispensing mechanism and the secondary dose dispensing mechanism may be linked or coupled by the engagement between the first and the second engagement section such that the actuation movement leads to actuation of the primary dose dispensing mechanism and the secondary dose dispensing mechanism. Actuation of the secondary dose dispensing mechanism automatically disengages the first and the second engagement section such that the actuation link is automatically disconnected.

The drug delivery device may be configured such that a set dose of the secondary medicament is dispensed prior to a set dose of the primary medicament when the actuator is operated. According to a further embodiment, the actuator has a pressing face configured to engage a pressure receiving section of the primary dose dispense mechanism and arranged such that the actuation movement of the actuator closes a gap between the pressing face and the pressure receiving section so that the actuation movement is transferred to the pressure receiving section. The pressure receiving section may be connected to the primary dose dispensing mechanism such that the actuation movement of the actuator is transferred to the primary dose dispensing mechanism and the primary dose dispensing mechanism is activated such that a set dose of the primary medicament is dispensed. Thereby, sequential delivery of the secondary medicament and the primary medicament may be achieved. Not before the gap is closed, the primary dose of medicament is dispensed. However, the actuation movement of the actuator is transferred to the secondary dose dispensing mechanism of the secondary drug delivery assembly before the gap is closed. Accordingly, when the gap is open and the actuator is moved with the actuation movement, the actuation movement is transferred to the actuation collar. The actuation movement, however, is not yet transferred to the pressure receiving section because the gap is open. Due to the actuation movement, the pressing face moves towards the pressure receiving section such that the gap is closed. When the pressing face reaches the pressure receiving section, it abuts the pressure receiving section such that movement of the pressing face is transferred to the pressure receiving section such that the primary dose dispensing mechanism is actuated. As a result, the secondary medicament is injected prior to the primary medicament. This effectively provides for the sequential delivery of two medicaments in one injection step. Accordingly, the gap has a delay function regarding the activation of the primary dose dispense mechanism wherein the secondary dose dispensing mechanism may be actuated before the primary dose dispensing mechanism is actuated.

According to a further embodiment, a biasing member may be configured to urge the actuator in a proximal direction with respect to the housing. In connection with the above described delay function, the patient may release the actuator such that it moves in proximal direction thereby relieving the engagement between the first engagement section and the second engagement section. This supports the resetting movement of the setting element.

Preferably, the engagement sections are configured for meshed engagement. In addition, the actuation collar may be configured such that the actuating movement of the actuation collar causes engagement with the secondary dose dispensing mechanism such that the secondary dose dispensing mechanism is activated.

In a further embodiment, the first and the second engagement section are configured such that the first and the second engagement section are urged to disengage when the actuator is moved in a direction relative to the actuation collar opposite to the actuation movement. This may be supported by a biasing member arranged within the housing which is configured to urge the actuator in proximal direction.

For effective disengagement, the first engagement section and the second engagement section may each be provided with a cam feature configured to cause disengagement of the first and second engagement section when the cam features are urged towards or moved against each other, such that the cam features engage and are pressed against each other.

According to a further embodiment, the first engagement section and the second engagement section may each comprise a toothed gear rack. The teeth may respectively comprise an abutment surface, wherein the abutment surfaces may be arranged such that they are aligned perpendicular to the axis of the actuation movement so that the actuation movement is effectively transferred from the first engagement section to the second engagement section.

According to a further embodiment, the first and/or the second engagement section may each have a chamfered flank on the backside of the abutment surface. Preferably, the chamfered flank of the first engagement section is arranged such that it substantially faces the proximal end of the housing while the chamfered flank of the second engagement section is directed to the distal end of the housing. The chamfered flanks may constitute the above described cam feature.

To prevent an improper disengagement of the first and the second receiving section, the first and the second engagement sections may be respectively connected to a latching portion. The latching portions may be configured to be driven into latching engagement when the setting element is moved from the first position into the second position, preferably by rotation. Accordingly, when the setting element drives the actuation collar into engagement with the actuator such that the actuation movement of the actuator can be transferred to the actuation collar, the latching elements engage. This helps to reduce the likelihood of disengagement of the first and the second engagement section and avoids consequences of mechanical impacts, e.g. when the patient drops the device. Each of the latching portions on the first and the second engagement section may be configured to extend substantially parallel to the first longitudinal axis. Latching elements may be provided in the latching portions which prevent relative rotational movement between the first and the second engagement section. When the first and the second engagement sections are engaged, the latching portions provide for a resisting force such that the first and the second engagement section are rotationally constrained in a releasable manner with respect to each other.

According to a further embodiment, the actuation collar comprises at least one protruding rib, preferably extending parallel to a commonly shared rotation axis of the setting element and the actuation collar. The protruding rib may be configured to engage at least one groove formed on the actuator and extending parallel to the first longitudinal axis. The arrangement of the groove and the rib may be opposite as well with the rib provided on the actuator and the groove provided on the actuation collar. The latching portions may be configured such that they engage each other in a snap-like manner. Such snap connection is beneficial, e.g., in terms of securing the engagement between the first and the second engagement section. A snap connection may also be beneficially used to give the user a tactile and/or sensible feedback indicating that the mechanical link between the first and the second engagement section is established.

The latching portions may be configured to disengage when the setting element is moved from the second into the first position. The latching portions may be configured such that the force required to disengage the latching portion corresponds to the force provided by the biasing member of the secondary drug delivery assembly for the resetting movement.

According to a further embodiment, the housing may comprise a locking element configured to rigidly engage the first and/or the second drug delivery assembly and to be detachably received within the housing. The housing may comprise at least two housing parts configured to rigidly receive the locking element when the housing parts are assembled. The locking element may be configured to be attached to drug delivery assemblies that have already passed approval procedures before the competent authorities. The locking element may be configured to rigidly engage the first and/or the second drug delivery assembly so that the first and/or the second drug delivery assembly is/are rotationally and/or longitudinally constrained with respect to the housing when received in the respective receiving section. The locking element may be configured as a coupling element, a locking or coupling collar, a spacer or an insert.

The drug delivery assemblies may comprise at least two housing parts wherein the locking element is adapted to be attached to attachment means provided on the drug delivery assembly housing parts for mutual attachment of the two housing parts. In other words, the locking element may be adapted to be fixed to attachment means on the drug delivery assembly wherein those attachment means are normally used to assemble the single parts of the drug delivery assembly. Here, the locking element may serve as a spacer, for example. Furthermore, with the locking element attached, the relative position between the primary drug delivery assembly and the secondary drug delivery assembly can be efficiently secured. Accordingly, the locking element may also serve as coupling element.

Preferably, the drug delivery device comprises at least one cartridge containing a medicament.

According to another embodiment a drug delivery device comprises a housing retaining a primary drug delivery assembly configured to receive a primary reservoir containing a primary medicament and a secondary drug delivery assembly configured to receive a secondary reservoir containing a secondary medicament, wherein the primary drug delivery assembly comprises a primary dose setting mechanism for setting a dose of the primary medicament and wherein the secondary drug delivery assembly comprises a secondary dose setting mechanism for setting a dose of the secondary medicament, wherein the secondary dose setting mechanism comprises a biasing member adapted to reset the secondary dose setting mechanism in a resetting movement and a trigger button for releasing the biasing member, wherein the trigger button is movable from a first into a second position. The device further comprises a setting element movable between a first position and a second position and connected to the secondary dose setting mechanism such that during the resetting movement of the secondary dose setting mechanism, the setting element is moved from the second position into the first position. An actuator is movable relative to the housing, wherein the actuator engages a primary dose dispensing mechanism of the primary drug delivery assembly during an actuation movement such that a set dose of the primary medicament is dispensed through a dispense interface, wherein the actuator comprises a first engagement section configured to engage a second engagement section provided by an actuation collar such that the actuation movement of the actuator is transferred to the actuation collar. The actuation collar is moveable relative to the actuator between a first position where the first engagement section and the second engagement section are not engaged and a second position relative to the actuator where the first engagement section and the second engagement section are engaged such that the actuation movement of the actuator is transferred to the actuation collar such that the actuation collar engages the trigger button and moves the trigger button into the second position. When the trigger button moves towards the second position, the trigger button releases the biasing member, wherein the biasing member is connected to the setting element such that the biasing member moves the setting element from the second into the first position when the biasing member relaxes, wherein the setting element is configured to drive the actuation collar out of engagement with the actuator when moving from the second position into the first position.

According to a further embodiment of the above drug delivery device, the secondary drug delivery assembly comprises a secondary dose dispense mechanism, wherein the secondary dose dispense mechanism is actuated when the trigger button is moved from the first into the second position such that a dose of the secondary medicament is dispensed. In a further embodiment, the biasing member is adapted to drive a drive member in axial direction when the biasing member is released, wherein displacement of the drive member forces a bung or the like in the secondary reservoir in distal direction such that secondary medicament in the secondary reservoir is driven out of the secondary reservoir. The biasing member may be connected to the setting element such that it is prestressed when the setting element is moved from the first into the second position.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Trp(O2)25, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following, aspects of the disclosure will be described by way of examples and with reference to the schematic drawings in which:

FIG. 1 shows in a perspective exploded view the inventive drug delivery device;

FIGS. 2a to 2c show a single dispense interface hub and the attachment to the housing of FIG. 1;

FIGS. 4a to 4d show parts of the drug delivery of FIG. 1 during a dose setting and dose dispensing sequence;

FIGS. 5a, 5b show a setting sequence of the secondary dose setting mechanism;

FIGS. 7a to 7c show in a perspective view a further detail of the drug delivery device.

Figure 3:
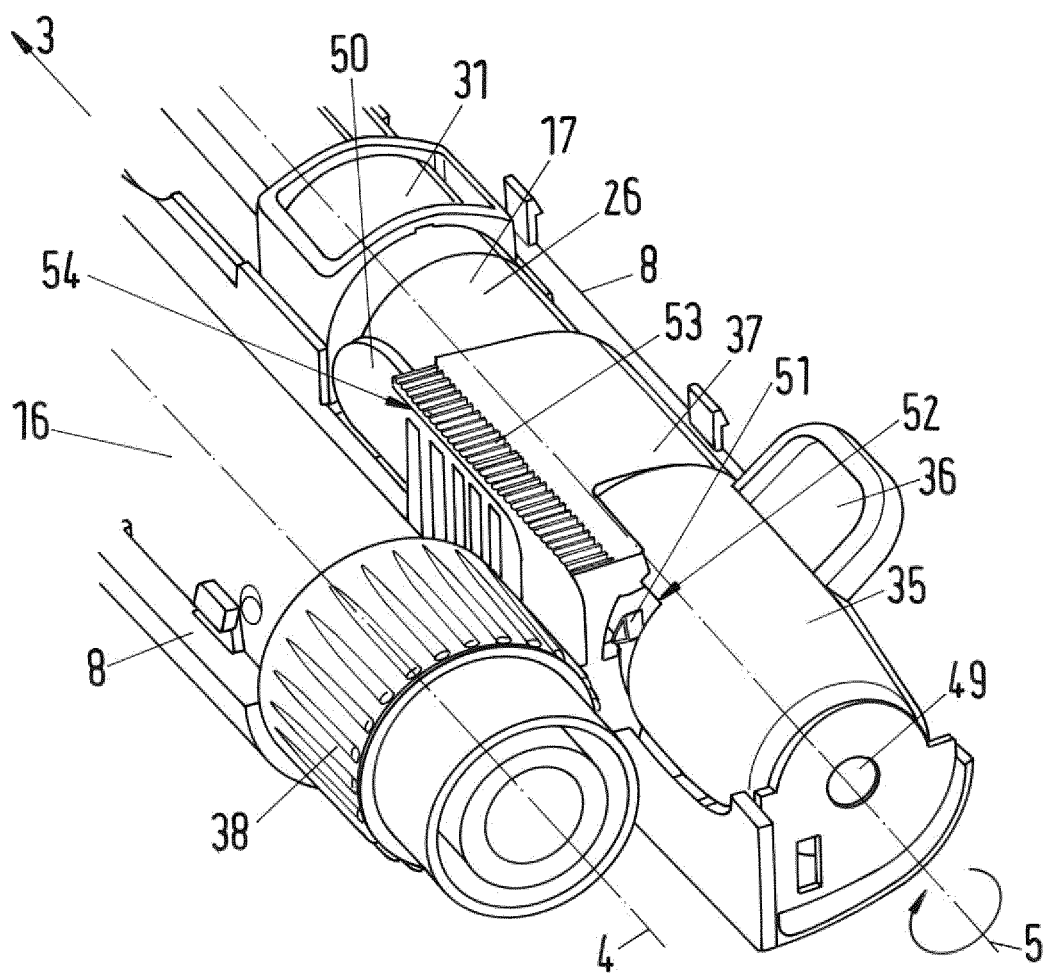
FIG. 3 shows in perspective view a portion of the drug delivery device of FIG. 1 with a part of the housing removed.

FIG. 1 shows of a drug delivery device 1 with a proximal end 2 and a distal end 3. A first longitudinal axis 4 and a second longitudinal axis 5 run in a parallel relationship parallel to a longitudinal axis 6 of a housing 7. The housing 7 comprises a first upper half shell 8 and a second lower half shell 9.

The first half shell 8 and the second half shell 9 are connectable at side edges 10, 11. When the drug delivery device 1 is assembled, first side edges 10 of the first half shell 8 engage second side edges 11 of the second half shell 9 and the first and the second half shell 8, 9 accommodate the majority of components disposed between the first half shell 8 and the second half shell 9 in FIG. 1 as explained further below.

The first side edges 10 and the second side edges 11 are provided with corresponding snap features 12 and 13 which ensure a fixed installation of the first and second half shell 8, 9. In an exemplary embodiment, each of the half shells 8, 9 is provided with eight snap features 12, 13 at their side edges arranged such as to engage its respective counterpart on the other of the half shells 8, 9.

A first receiving section 14 of the housing 7 extends from the proximal end 2 to the distal end 3 of the housing 7 and is disposed substantially parallel to a second receiving section 15 of the housing 7. The first longitudinal axis 4 runs through the first receiving section 14 while the second longitudinal axis 5 runs through the second receiving section 15.

If the drug delivery device 1 is assembled, the first receiving section 14 retains a primary drug delivery assembly 16 and the second receiving section 15 retains a secondary drug delivery assembly 17. The primary drug delivery assembly 16 is a pen-type injector of the kind that provides for administration by injection of medicinal products from a multi dose cartridge. The primary drug delivery assembly 16 comprises a primary assembly housing 18 with a piston rod (not shown) having a screw thread, an insert which is located in the primary assembly housing 18 and through which the piston rod may rotate. The insert is secured to the housing 18 and the piston rod is threadedly engaged with an inner thread provided on the insert. A drive sleeve (not shown) is rotatable with respect to the piston rod during dose setting (including dose cancelling) and is axially displaceable but not rotatable with respect to the piston rod during dose delivery. A dose dial sleeve 19 (see FIG. 4a) is accommodated in and rotatable with respect to the primary assembly housing 18. The dose dial sleeve 19 engages the primary assembly housing 18 with an outer screw thread which engages an inner screw thread on the primary assembly housing 18 or a threaded housing insert such that rotation of the dose dial sleeve 19 relative to the primary assembly housing 18 leads to axial displacement of the dose dial sleeve 19 relative to the primary assembly housing 18. The dose dial sleeve 19 is provided with a series of numbers on its outer surface which are visible through an opening or window of housing 18.

A primary dispense button 20 is located on the drive sleeve at its proximal end. The primary assembly housing 18 contains a clutch means (not shown) which upon depression of the primary dispense button 20 allows relative rotation between the dose dial sleeve 19 and the drive sleeve. A spring (not shown) is provided biasing the clutch and the primary dispense button 20 into a position releasably coupling the dial sleeve 19 and the drive sleeve such that they are rotationally constrained. The piston rod and an internal surface of the drive sleeve are in a threaded engagement such that the drive sleeve drives the piston rod upon longitudinal displacement of the drive sleeve during dose dispensing.

The piston rod extends in axial direction of the primary assembly housing 18 and is provided with a pressure foot at its distal end. At the distal end of the primary assembly housing 18, a cartridge holder 21 is releasable attached to the primary assembly housing 18. The cartridge holder 21 receives a primary cartridge 22 (primary container) containing a primary medicament. The distal end of the primary cartridge 22 is closed with a septum.

For setting a dose, the operator must first select a dose. To set a dose, the dose dial sleeve 19 is rotated by manipulating a distal end section configured as a dose setter 23. The dose setter 23 is rotated until the desired dose value is visible through a first window 24 in the primary assembly housing 18 and a second window 25 or opening in the first half shell 8. When the drug delivery device 1 is assembled, the first window 24 and the second window 25 coincide. The rotation of the dose setter 23 moves the dose dial sleeve 19 in proximal direction with respect to the housing 18 in a helical movement.

The drive sleeve rotates together with the dose dial sleeve 19 relative to the piston rod. The piston rod does not rotate during dose setting. The drive sleeve is carried in proximal direction along the piston rod by the dose dial sleeve as the dose dials sleeve 19 moves out of the primary assembly housing 18.

Once the desired dose has been set, in order to deliver the dose, the primary dispense button 20 is moved in distal direction. When the primary dispense button 20 is depressed, clutch means provided between the dose dial sleeve 19 and the drive sleeve allow relative rotation between these components and rotationally constrain the drive sleeve to housing 18 so that longitudinal displacement of the primary dispense button 20 in the distal direction causes the drive sleeve to move axially towards the distal end of the primary drug delivery assembly 16, while the dose dial sleeve 19 rotates back into the housing 18. Since the piston rod is threaded to the drive sleeve, the piston rod is rotated through the insert in distal direction, thereby advancing a piston in the primary cartridge 22 such that the set dose of the primary medicament is dispensed through a dispense interface fluidly connected to the primary cartridge 22 at its distal end.

The secondary drug delivery assembly 17 is also a pen-type injector with a user operable dose setting mechanism. The secondary drug delivery assembly 17 is known in the art as being of the power assisted injector type and comprises a prestressable biasing member (not shown) configured to relax and to automatically dispense a set dose of a secondary medicament when a secondary dose dispensing mechanism is actuated. A secondary assembly housing 26 accommodates the secondary dose setting mechanism, which comprises a dose knob 27 rotatably coupled to the secondary assembly housing 26 at its proximal end. An outer screw thread 28 is provided at the distal end of a secondary assembly housing 26. A cartridge holder 29 is located at the distal end of the secondary drug delivery assembly 17 and receives a disposable secondary cartridge 30 (secondary container) containing a secondary medicament. The distal end of the secondary cartridge 30 is closed with a septum while a bung (not shown) seals the proximal end of the cartridge.

In the secondary assembly housing 26 there is arranged the secondary dose setting mechanism and a secondary dose dispensing mechanism. The secondary dose dispensing mechanism includes a trigger button (reference numeral 50 in FIG. 3) that is movable from a proximal to a distal position relative to the secondary assembly housing 26. When the trigger button is moved into the distal position, the secondary dose dispensing mechanism is actuated.

A biasing element such as a torsion spring (not shown) is provided within the secondary assembly housing 26 and is coupled to a drive member (not shown). The dose setting knob 27 is coupled to the torsion spring such that during a setting movement to set a dose of the secondary medicament for injection, by rotating the dose knob 27 relative to the secondary assembly housing 26 in a first direction, the spring is prestressed. Actuation of the trigger button releases the spring. By releasing the spring, the spring forces the drive member to move through the secondary assembly housing 26 in distal direction. The displacement of the drive member is proportional to the aforesaid dose, which corresponds to the degree of rotation of the dose knob 27 relative to the secondary assembly housing 26.

Between the cartridge holder 29 and the secondary assembly housing 26 a locking element configured as a collar 31 is provided. As in the depicted embodiment the second drug delivery assembly 17 is of the power assisted injector type, the collar 31 is referred to as "auto collar" 31. The auto collar 31 has an internal screw thread provided at its proximal end for attachment to the external thread 28 at the distal end of the secondary assembly housing 26 and an external thread provided at its distal end for attachment to the cartridge holder 29 which is provided with a corresponding internal thread at its proximal end. The setup of the internal screw thread of the auto collar 31 corresponds to the internal thread of the cartridge holder 29, while the external thread of the auto collar 31 corresponds to the external thread of the secondary assembly housing 26. Thereby, the auto collar 31 constitutes an inserted intermediate piece that lengthens the overall length of the secondary drug delivery assembly 17 in axial direction.

The secondary drug delivery assembly 17 is usually produced and delivered by the manufacturer with the internal screw thread of the cartridge holder 29 directly engaging the outer screw thread 28 of the secondary housing assembly 26, hence, without the auto collar 31. In the depicted embodiment, the auto collar 31 is interposed therebetween to lengthen the overall length of the secondary drug delivery assembly 17, i.e. to adapt it to the length of the primary drug delivery assembly 16. It goes without saying that the provision of the auto collar may be omitted or that a similar means may be provided for the primary drug delivery assembly if required. In addition, the dimensions of the housing or its components may be adapted to fit various sizes of the primary and secondary drug delivery assemblies.

The cartridge holder 29 of the secondary drug delivery assembly 17 is provided with a window 32 through which a cartridge plunger 33 is visible which has been added to the secondary drug delivery assembly 17 as the auto collar 31 has. The cartridge plunger 33 is axially movable received within the cartridge holder 29. The cartridge plunger 33 is a sleeve-like element having a proximal end and may be driven in distal direction by the drive member of the secondary dose dispensing mechanism (for example a piston rod) wherein the drive member extends through an inner opening extending through the auto collar 31 to push against the proximal end of the cartridge plunger. The distal end of the cartridge plunger 33 has a distal opening which receives a proximal section of the secondary cartridge 30. The proximal end of the opening is provided with a pressure foot which abuts the bung of the secondary cartridge 30 when the cartridge plunger 33 moves distally with respect to the secondary cartridge 30. The cartridge plunger 33 forces the bung in distal direction when driven by the drive member such that the secondary medicament from the secondary cartridge 30 is expelled through the dispense interface attached to the distal end of the housing.

In the depicted embodiment, the original cartridge (not shown) of the power assisted-injector 17 has been replaced by the secondary cartridge 30 which is regarding its outer-diameter and inner volume smaller than the original cartridge. When the cartridge plunger 33 is displaced in distal direction by the drive member of the secondary dose mechanism, the cartridge plunger 33 starts to cover the outer surface of the secondary cartridge 30 and a dose of the secondary medicament is forced out of the secondary cartridge. Because the secondary cartridge 30 is smaller than the original cartridge the herein shown power assisted injector has been layed out such that a dose that is set with the secondary dose setting mechanism is larger than the dose that is actually dispensed upon actuation. In other words, the size of the secondary cartridge 30 has been chosen with regard to its inner diameter that the amount of secondary medicament that is expelled during dispensing the dose is half the dose that set with the dose knob 27.

The outer surface of the cartridge plunger 33 is provided with other visual indicators. As the displacement of the cartridge plunger 33 relative to the secondary cartridge 30 corresponds to the amount of secondary medicament being expelled from the secondary cartridge 30, the position of the cartridge plunger 33 relative to the secondary cartridge 30 indicates the patient the amount of secondary medicament that is left in the secondary cartridge 30. It is possible to provide a marking on the outer surface of the cartridge plunger, e.g. with a sticker, a label or the like. The marking gives the patient a visual indication of the decreasing filling level over a period of his treatment, e.g. through an opening or window in the housing. For example, a number of rings provided on the outer circumference of the cartridge plunger that may be arranged one behind each other in axial direction may indicate resp. present to the number of days, the patient has already used the device for his treatment. With each injection, the plunger moves in distal direction over a distance corresponding to the volume of medicament that is dispensed and an increasing number of rings becomes visible by moving into the field of vision though the window or opening in the housing. By a change of color in the rings, e.g. from blue to red, when the amount of medicament that is left in the cartridge reaches a minimum level, the patient is reliably informed about the upcoming depletion of the medicament.

The housing 7 further comprises an actuator 34 and setting element 35 with a lever 36 to enable the user to conveniently set a dose with the secondary medicament, an actuation collar 37 and a receiving element 38 for the dose setter 23 configured to be manipulated by the patient to set a dose of the primary medicament. The actuator 34 comprises an elongated bar 39 extending parallel to the first longitudinal axis 4 and an actuation section 40 which extends substantially perpendicular to the bar 39. The actuator 34 is mainly located in the first receiving section 14 and the bar 39 substantially extends between the primary drug delivery assembly 16 and the secondary drug delivery assembly 17. The actuator is slidably guided in the housing 7 by respective formed guidance section, which may include webs or the like (not shown). The receiving element 38 is located between the primary dispense button 20 and the actuation section 40. The actuation section 40 is located at the proximal end of the actuator 34. A button cap 41 is coupled to the proximal end of the actuation section 40.

A single dispense interface 42 is releasably attachable to the distal end 3 of the housing 7. The single dispense interface 42 is a needle hub having two proximal needles to pierce the septum of each of the primary cartridge 22 and the secondary cartridge 30, wherein the two proximal needles are fluidly connected to an attachment section 47 located at the distal end of the single dispense interface 42. An injection needle (not shown) is attachable to the attachment section 47 for injecting the primary medicament and the secondary medicament into the skin of a patient. A cap 43 is releasably attachable to the distal end of the drug delivery 1 to cover the distal end 3 of the drug delivery device 1 and the single dispense interface 42 when the device is not in use. Of course, the single dispense interface 42 could be configured as non-detachable, wherein the single dispense interface 42 is not removable from the housing 7 after having been attached. The drug delivery device 1 may then be provided as a disposable injection device. Such devices can be thrown away or recycled after the content of one or both of the medicaments has been exhausted.

In FIGS. 2a to 2c, the drug delivery device is from FIG. 1 is assembled together with the first half shell 8 and a second half shell 9 being attached to each other. The distal end of the primary cartridge 22 and the distal end of the secondary cartridge 30 are accessible. For attachment, the housing 7 and the single dispense interface 42 are provided with releasable locking features comprising a flexible snap feature 44 with an external bump 45. On the inside of the housing 7, the snap feature 44 has a projection (not shown) configured to engage a recess 46 provided on the dispense interface 42. As can be seen from FIGS. 2a to 2c, the proximal end of the dispense interface 42 is inserted into the distal end of the housing 7. During attachment, the section of the dispense interface 42 lying proximally from the recess 46 lifts resp. tilts the snap feature 44 as shown in FIG. 2b. As a result, the snap feature 44 visibly extends from the upper surface of the housing 7 indicating that the dispense interface is not yet sufficiently inserted into the housing 7. The snap feature 44 gives visually impaired patients a reliable tactile feedback regarding a proper attachment process, in particular.

When the dispense interface 42 is properly attached to the housing 7, the two proximal needles (not shown) of the dispense interface 42 pierce the septa of the primary cartridge 22 and the secondary cartridge 30. At the distal end of the dispense interface 42, the attachment section 47 for attachment of the injection needle is provided. The attachment section 47 is configured as an outer thread with a central opening 48. The central opening 48 is configured to receive a proximal end of an injection needle wherein attachment of the injection needle establishes fluid communication with both of the proximal needles of the single dispense interface. With the distal end of the injection needle the primary medicament and the secondary medicament are injected through the skin of a patient. When the dispense interface 42 is properly attached to the drug delivery device 1 and when the distal injection needle is attached to the attachment section 47, fluid connection between the primary cartridge 22, the secondary cartridge 30 and the injection needle is established.

The dispense interface 42 is properly attached to the housing 7 when the 44 snap feature snaps into the recess 46. Then, the outer surface at distal end of the housing 7 is flat and the outer surface of the snap feature 44 (with the exception of the external bump 45) lies substantially flush with the outer surface of the housing 7 which indicates that the dispense interface 42 is properly attached to the drug delivery device.

The bump feature 45 is provided to engage a corresponding protrusion or recess (not shown) in the inner surface of the cap 43 when the cap 43 is attached to the distal end of the housing 7 (see FIG. 1), thereby ensuring the tight fit of the cap 43 on the housing 7.

FIG. 3 shows the primary drug delivery assembly 16 and the secondary drug delivery assembly 17 received in the first half shell 8. The setting element 35 is attached to the dose knob of the secondary drug delivery assembly 17 such that rotation of the setting element 35 about the second longitudinal axis 5 is directly transferred to the dose knob. A proximal end of the setting element 35 is received within a closed ring 49 provided by the first half shell 8 to ensure that the axis of rotation of the setting element 35 remains properly aligned. This ensures that the setting element 35 does not tilt before, during and after rotation of the setting element 35 around the second longitudinal axis 5. The auto collar 31 rigidly engages the secondary drug delivery assembly 17 and is also detachably received within the housing, wherein inner surfaces of first half shell 8 and the second half shell comprise a number of webs which rigidly accommodate the actuation collar 31 when the housing parts 8, 9 are assembled. Thereby, the secondary drug delivery assembly 17 is rotationally and axially constrained by the auto collar 31 with respect to the housing 7. This ensures the correct position of the secondary drug delivery assembly 17 within the housing and relative to the primary drug delivery assembly 16.

The receiving element 38 is configured as a user-operable dose setter with a serrated outer surface and connected to the dose setter of the primary drug delivery assembly such that rotation of the receiving element 38 relative to the primary assembly housing is directly transferred to the dose setter 23.

The secondary dose dispensing mechanism of the secondary drug delivery assembly 17 comprises the aforementioned trigger button 50. A projection 51 is provided on the outside of the secondary assembly housing 26 and is normally used to indicate a set dose by indicating a relative rotational position between the projection 51 and the dose knob. The setting element 35 is provided as a cap and is put on the dose knob, wherein the inner surface of the cap has a number of ribs, bump features or the like that engage recesses in the outer surface of the dose knob such that rotation of the setting element 35 is transferred to the dose knob.

The setting element 35 has a cutout 52 which is an axially extending recess, slot or an axially stepped back portion in the sleeve-like distal section of the setting element 35. In other words, at the distal end section of the setting element 35, a circular sector of a distal sleeve section of the setting element 35 has been cut out. The cutout 52 receives the projection 51. The cutout 52 of the setting element 35 extends over a sector of the setting element 35 in circumferential direction. The length of the circular sector which the cutout 52 extends over is chosen such that the setting element 35 is rotatable between a first position in which the projection 51 abuts an inner side wall of the cutout 52 and a second position in which an opposite inner side wall of the cutout 52 abuts against the opposite side of the projection 52. The inner side walls serve in as rotational abutment surfaces. The projection 51 limits the settable dose of the secondary medicament to a maximum dose.

The actuation collar 37 is provided with a second engagement section 53 formed as a toothed rack and is put over the secondary drug delivery assembly 17. A cutout 54 forms a recess in the actuation collar 37, the recess extending from a distal end of the actuation collar 37 in proximal direction. The cutout 54 partly receives the trigger button 50. The cutout 54 in the actuation collar 37 is wider that the width of the trigger button 50. Displacement of the actuation collar 37 in distal direction causes the trigger button 50 to move in the same direction by what the secondary dose dispensing mechanism is actuated and the drive member of the secondary drug delivery assembly 17 urges the cartridge plunger 33 in distal direction.

FIGS. 4a to 4d show the dose setting and injection process with a drug delivery device 1. The actuator 34 comprises a first engagement section 55 formed on the bar 39 and is rotationally constrained in the housing but axially moveable with respect to the housing in distal direction.

The first engagement section 55 and the second engagement section 53 each have a toothed gear rack for mutual meshed engagement. When the engagement sections 55, 53 are engaged, longitudinal displacement of the actuator 34 in distal direction 3 is transferred to the actuation collar 37 so that the actuation collar 37 is moved distally, too.

In FIG. 4a, the first engagement section 53 and the first engagement section 55 are not engaged. Accordingly, the actuator 34 is free to move relative to the actuation collar 37 in axial direction. Setting a dose with the primary medicament, requires the patient to rotate the receiving element 38 which causes the dose dial sleeve 19 to move in proximal direction 2. The actuator 34 is connected to the receiving element 38 so that the proximal displacement of the receiving element 38 moves the actuator 34 in proximal direction relative to the secondary engagement section 53 and the housing 7. Accordingly, during setting of a primary medicament dose, the dose setting mechanism of the primary drug delivery assembly 16 and the secondary drug delivery assembly 17 are not mechanically linked which prevents mutual interferences.

When the dose in the primary drug delivery assembly has been set as depicted in FIG. 4a, the user rotates the setting element 35 by operating the lever 48 so that the setting element 35 is rotated about the second longitudinal axis 5 from a first position as shown in FIG. 4a to a second position as shown in FIG. 4b. This rotational movement of the setting element is referred to as the setting movement and is indicated with the curved arrow in FIG. 4b.

When the setting element 35 is rotated from the first position into the second position, the setting element 35 transfers rotational movement onto the actuation collar 37. As the actuation collar 37 is arranged coaxially with the setting element 35 it rotates about the same axis 5 as the setting element 35. Rotation of the actuation collar 37 brings its second receiving section 53 into engagement with the first receiving section 55. When the setting element 35 reaches the second position, the first engagement section 55 and the second engagement 53 are brought into engagement. Accordingly, the second position of the setting element 35 corresponds to the engagement between the first engagement section 55 and the second engagement section 53. The setting element 35 has to be rotated entirely from the first into the second position to couple the actuator 34 to the actuation collar 37 so that the drug delivery device is properly operable.

When the secondary dose is set and the actuator 34 is operationally coupled to the actuation collar 37, the patient operates the actuator 34 by displacing the actuator 34 in a longitudinal movement in distal direction 3. This movement is referred to as the actuation movement. The actuation movement is transferred to the actuation collar 37 through the first and second engagement section 55, 53 so that the actuation collar 37 is moved in distal direction and urges the trigger button 50 of the secondary drug delivery assembly 17 in distal direction such that the secondary dose dispensing mechanism is actuated and the set dose of the secondary medicament is expelled under the force of the prestressed biasing member. Accordingly, the setting movement leads to an adjustment of the set dose of the secondary medicament and to the coupling of the actuating movement to the secondary dose dispense mechanism. Only when the setting element is rotated all the way from its first into its second position the set dose of the secondary medicament can be dispensed. In connection with the projection 51 (FIG. 3) the variable dose setting mechanism of the secondary drug delivery assembly 17 is turned into a fixed dose setting mechanism.

As the biasing member (torsion spring) of the secondary dose dispensing mechanism relaxes, it rewinds the dose knob into its initial position. This movement is transferred to the setting element 37, which is set from the second position into the first position as shown in FIG. 4c. This movement is referred to as the resetting movement indicated with the curved arrow in FIG. 4c. When the setting element 37 rotates in the direction opposite to the setting movement, it transfers the rotational movement again onto the actuation collar 37 so that the actuation collar 37 is rotated in the same direction. Thereby, the first engagement section 55 and the second engagement section 53 are disengaged again. The actuator 34 is then again free to move relative to the actuation collar 37 in longitudinal direction of the housing 7 and can be further displaced in distal direction by the user as shown in FIG. 4d so that the said dose of the primary medicament is dispensed.

FIGS. 5a and 5b show the engagement process between the first engagement section 55 and the second engagement section 53. When the setting element 35 is rotated during the setting movement as indicated by the arrow 56, the setting element 35 rotates the actuation collar 37 in the same direction such that first engagement section 55 and the second engagement section 53 engage as displayed in FIG. 5b. Each of the engagement sections 55, 53 is provided with a latching portion. The latching portions of the first engagement section 55 and the second engagement section 53 are driven into latching engagement by the setting movement 56. For that purpose, the actuation collar 37 comprises a protruding rib 57 which engages an axially extending groove 58 formed on the bar 39. The protruding rib 57 snaps into the groove 58 with a perceivable sound when the first engagement section 55 and the second engagement section engage 53. Distally oriented flat surfaces of the teeth of the first engagement section 55 and proximally oriented flat surfaces of the teeth of the second engagement section 53 extend perpendicular to the rotational axis of the setting movement 56. Accordingly, these abutment surfaces transmit the actuation movement of the actuator 34 onto the actuation collar 37 but do not prevent the first and second engagement sections 55, 53 from improper disengagement. The rib/groove connection 57/58, however, prevents accidental disengagement between the actuation collar 37 and the actuator 34.

The distally oriented side of the teeth of the second engagement section 53 and the proximally oriented side of the teeth of the first engagement section 55 each have chamfered flanks so that when the actuator 34 moves in a direction opposite the actuation movement, respectively in proximal direction with respect to the actuation collar 37, the chamfered flanks engage and urge the first engagement section 55 and the second engagement section 53 to disengage. On the contrary, the flat surfaces on the respective backside of the chamfered flanks prevent lateral forces that could disengage the first and second engagement section 55, 53.

Figure 6:
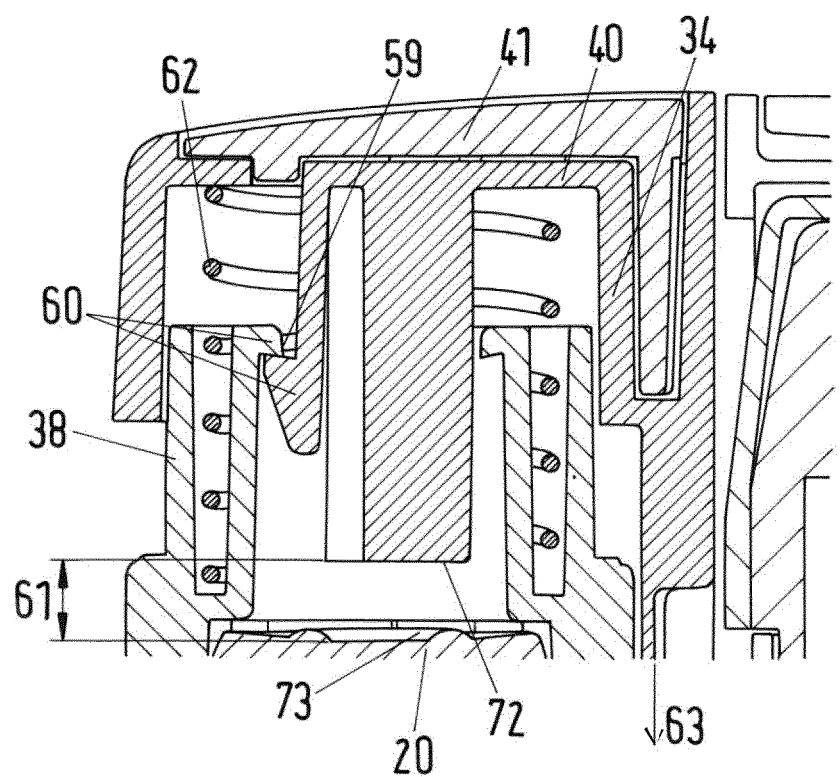
FIG. 6 shows a cross-sectional view of a detail of the drug delivery device.

FIG. 6 is a sectional view of the proximal end of the actuator 34. The button cap 41 is attached to the proximal end of the actuation section 40. The receiving element 38 is attached to the dose setter of the primary drug delivery assembly. The receiving element 38 is a sleeve-like component with a through-hole 59 through which a projecting of the actuation section 40 extends towards the primary dispense button 20. The distal end of the projection serves as a pressing face 72. The actuator 40 is secured to the receiving element 38 by a snap feature 60 which prevents removal of the actuation section 40 from the receiving element 38. However, the pressing face 72 is initially arranged at a distance with respect to the primary dispense button 20 such that a gap 61 is present between the proximal end of the primary dispense button 20 and the pressing face 72. A biasing member in form of a spring 62 is inserted into the receiving element 38. The spring engages a distal inner surface of the actuation section 40 and urges the actuator 34 in proximal direction with respect to the receiving element 38. The actuator 34 is movable with respect to the receiving element 38 between a first position, in which the pressing face 72 does not contact the primary dispense button 20 and a second position, in which the pressing face 72 makes contact with the primary dispense button 20.

When a dose with the primary medicament has been set and the first and the second engagement sections have been driven into engagement by the setting movement applied to the setting element, the actuator 34 is urged in distal direction by the patient from the first position into the second position with respect to the receiving element 38. In a first phase of the actuation, the actuating movement 63 of the actuator 34 is directly transferred to the actuation collar which engages the trigger button of the secondary drug delivery assembly so that the set dose of the secondary medicament is dispensed. Further displacement of the actuator 34 in distal direction closes the gap 61 so that the pressing face and the proximal surface of the primary dispense button 20, which serves as a pressure receiving section 73, make contact and the actuation movement 63 of the actuator 34 is transferred to the primary dispense button 20 which activates the primary dose dispense mechanism. This gap 61 causes a delay in the activation of the primary dispense mechanism compared to the secondary dose dispense mechanism. As a result, the set dose of the secondary medicament is dispensed prior to dispense of the primary medicament. The result is a mechanical control which provides for a reliable sequential delivery of the primary medicament and the secondary medicament in one application procedure.

Displacement of the actuation collar in distal direction is limited by the trigger button. When the trigger button has been displaced by the actuation collar to the maximum possible displacement in the first phase of the actuation, resp. delivery sequence, the actuator 34 cannot be displaced further in distal direction. In this situation, the gap 61 is so broad such that the actuation collar reaches the maximum possible distal displacement before the gap 61 is closed. Further displacement of the actuator 34 in distal direction is prevented. The user has to release pressure on the actuator 34 such that under the force of the spring 62 the actuator 34 is moved in proximal direction with respect to the receiving element 38. As a result, the chamfered flanks of the first receiving section 55 and the second receiving section 53 engage and the actuator 34 and the actuation collar 37 are urged to disengage supported by the force induced by the resetting movement. After that, the actuator is free to move in axial direction relative to the actuation collar and the patient may fully displace the actuator 34 in distal direction so that the gap 61 is closed and the actuation movement 63 is transferred to the primary dispense button. The set dose of primary medicament is then dispensed, wherein the set dose of secondary medicament is dispensed prior to the primary medicament.

FIGS. 7a to 7c display the resetting process. In the embodiment of FIGS. 7a to 7c, the length of the cutout circular sector 52 is larger than a projecting section 64 of the actuation collar 37 in circumferential direction about the second longitudinal axis 5. This allows relative rotational movement between the setting element 35 and the actuation collar between two relative rotational positions. The projecting section 64 is located in the cutout 52. In FIG. 7a, the setting element 35 is in its second position after having been rotated from the first position into the second position during the setting movement. In FIG. 7a, the setting element 35 is also in a first relative rotational position with respect to the actuation collar 37. When the set dose of secondary medicament is dispensed, the biasing member of the secondary dose setting mechanism rewinds the dose setting element 35 from the second position towards its initial first position (FIG. 7b) in the resetting movement 65 about the second longitudinal axis 5. As the length of the cutout circular sector is larger than the projecting section 64 in circumferential direction, the setting member 35 initially rotates relative to the actuation collar 37 into a second relative rotational position with respect to the actuation collar 37. In the second relative rotational position, a rotational abutment surface 66 engages the projecting section 64. Rotational movement of the setting element 35 is then transferred to the actuation collar 37. The setting element 35 continues the resetting movement 65 until the setting element 35 reaches its first position again. During the final travel of the setting element 35, the setting element 35 drives the actuation collar 37 out of its engagement with the actuator 34 and then reaches it first position as shown in FIG. 7c. The afore described disengagement function advantageously uses the stored force of the secondary dose setting mechanism to disengage the mechanical connection between the primary dose dispensing mechanism and the secondary dose dispense mechanism.

The setting process may work in a similar way, wherein the process substantially may run backwards from FIGS. 7c to 7a. In circumferential direction opposite to the rotational abutment surface 66 is a further abutment surface (not shown), divided from the rotational abutment surface 66 by the cutout 52. Starting from FIG. 7c, the user would rotate the setting element in a setting movement opposite to the resetting movement 65. Due to the cutout 52, the setting element 35 starts to rotate from its first position towards its second position. Initially, the setting member 35 rotates relative to the actuation collar 37. Then, when reaching the first relative rotational position again, the further abutment surface in the cutout 52 engages a respective counter surface on the actuation collar 37, which is located rearwardly (in circumferential direction) to the side of the projection 64 that is engaged by the abutment surface 66 during resetting movement. Upon the engagement, the rotational setting movement of the setting element 35 is transferred to the actuation collar 37 such that the setting element 35 drives the actuation collar 37 in a rotational motion which leads to the engagement of the first engagement section and the second engagement section. Hence, the engagement between the first and the second engagement section 55, 53 can be delayed in the setting process. The cutout 52 is regarding its sectional area dimensioned such that the setting element 35 has to be rotated entirely into its second position to ensure that the setting element 35 is moved into the first relative rotational position and the first and the second engagement section are brought into engagement. In other words, the setting procedure, resp. the setting movement must be completed. Otherwise, the first and the second engagement section do not engage. This safely prevents the activation of the secondary dose dispensing mechanism if the setting element is not moved into the second position properly and ensures that only a predetermined fixed dose can be injected.

Figure 8A:
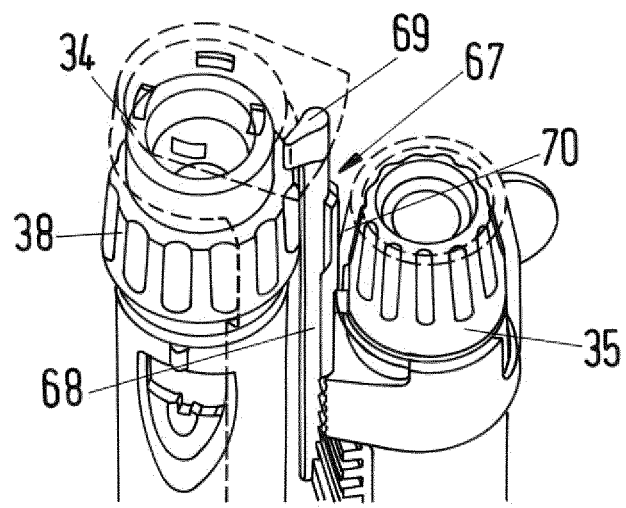
FIGS. 8a to 8b show in a perspective view parts of a drug delivery device in accordance with a second embodiment of the present disclosure.
Figure 8B:
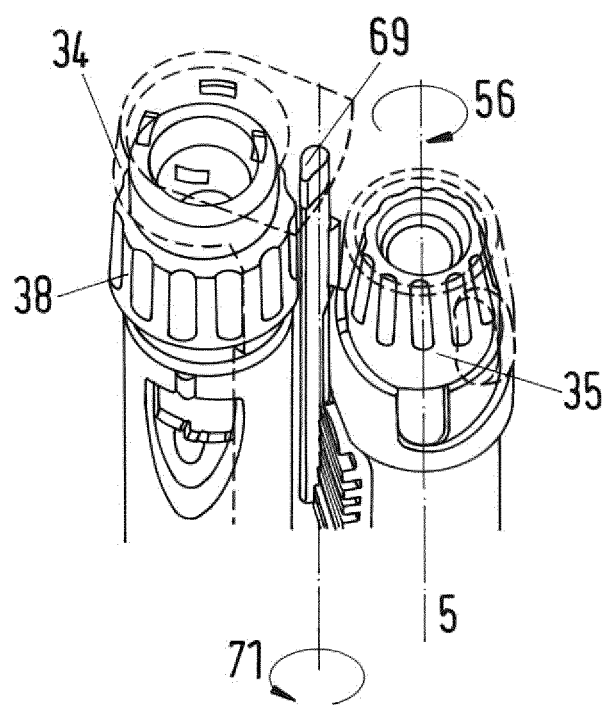

In the embodiment of FIGS. 8a and 8b, a locking unit 67 comprises a rod 68 with a distal end and a proximal end with a locking pawl 69 and a distal end. The locking unit 67 is rotatably arranged with respect to the housing between a locked position (FIG. 8a) and an unlocked position (FIG. 8b). In the locked position, the locking pawl 69 engages a free space or a gap between the actuator 34 and the receiving element 38. The locking pawl 69 blocks a movement of the actuator 34 towards the receiving element 38. As a result, the actuator 34 cannot be set from its first into its second position and the primary dose dispensing mechanism cannot be actuated by the actuator 34.

The locking unit 67 is rotatable about a longitudinal axis of the rod 68. A thrust area 70 extends from the rod 68 and is arranged such that when actuation collar 37 is driven into engagement with the actuator 34 by the setting movement 56 of the setting element 35, the actuation collar 37 engages the thrust area 70 and rotates the locking unit 67 about the longitudinal axis of the rod 68 (FIG. 8b). By rotation of the locking unit 67 (as indicated by the arrow 71), the locking pawl 69 is swung away from the actuator 34 so that displacement of the actuator 35 in distal direction with respect to the receiving element 38 is no longer prevented. This ensures that a set dose of the primary medicament cannot be dispensed without setting and injecting a fixed dose of the secondary medicament.

REFERENCE NUMERALS 1 drug delivery device
2 proximal end
3 distal end
4 first longitudinal axis
5 second longitudinal axis
6 longitudinal axis of housing
7 housing
8 first half shell
9 second half shell
10 first side edges
11 second side edges
12 snap features
13 snap features
14 first receiving section
15 second receiving section
16 primary drug delivery assembly
17 secondary drug delivery assembly
18 primary assembly housing
19 dose dial sleeve
20 primary dispense button
21 cartridge holder
22 primary cartridge
23 dose setter
24 first window
25 second window
26 secondary assembly housing
27 dose knob
28 outer screw thread
29 cartridge holder
30 secondary cartridge
31 locking element (auto collar)
32 window
33 cartridge plunger
34 actuator
35 setting element
36 lever
37 actuation collar
38 receiving element
39 bar
40 actuation section
41 button cap
42 single dispense interface
43 cap
44 snap feature
45 external bump
46 recess
47 attachment section
48 central opening
49 closed ring
50 trigger button 51 projection
52 cutout
53 second engagement section
54 cutout
55 first engagement section
56 setting movement
57 rib
58 groove
59 through-hole
60 snap-feature
61 gap
62 spring
63 actuation movement
64 projection section
65 resetting movement
66 rotational abutment surface
67 locking unit
68 rod
69 locking pawl
70 thrust area
71 rotation of locking unit
72 pressing face
73 pressure receiving section

The invention claimed is:

1. A drug delivery device comprising:
a housing retaining a primary drug delivery assembly and a secondary drug delivery assembly, the secondary drug delivery assembly comprising
  a secondary dose setting mechanism, wherein the secondary dose setting mechanism comprises a biasing member adapted to reset the secondary dose setting mechanism in performing a resetting movement;
an actuator movable relative to the housing, the actuator comprising
  a first engagement section configured to engage a second engagement section, the second engagement section provided by an actuation collar,
  wherein an actuation movement of the actuator is transferred to the actuation collar;
a dispensing interface, and
a setting element movable between a first position and a second position, wherein the setting element is connected to the secondary dose setting mechanism,
wherein during the resetting movement of the secondary dose setting mechanism, the setting element is moved from the second position into the first position,
wherein the setting element is configured to drive the actuation collar out of engagement with the actuator when the setting element is moved from the second position into the first position,
wherein the primary drug delivery assembly comprises a primary dose setting mechanism and is configured to receive a primary reservoir containing a primary medicament,
wherein the actuator engages a primary dose dispensing mechanism of the primary drug delivery assembly during the actuation movement to dispense a set primary dose of medicament through the dispense interface.

2. The drug delivery device according to claim 1, wherein the secondary drug delivery assembly comprises a secondary dose dispensing mechanism,
wherein the setting element is movable from the first position into the second position during a setting movement,
wherein the biasing member is prestressed by the setting movement, and
wherein by activation of the secondary dose dispensing mechanism, the biasing member is caused to relax and drives the setting element from the second position into the first position.

3. The drug delivery device according to claim 1, wherein the setting element and the actuation collar are disposed coaxially,
wherein the setting element is rotatable relative to the actuation collar between a first relative rotational position and a second relative rotational position, and
wherein during the resetting movement, the setting element is moved from the first relative rotational position into the second relative rotational position to rotationally engage the setting element with the actuation collar.

4. The drug delivery device according to claim 1, wherein the primary dose setting mechanism and the secondary dose setting mechanism are respectively directly operable.

5. The drug delivery device according to claim 1, wherein the primary drug delivery assembly comprises a primary dose setting mechanism and is configured to receive a primary reservoir containing a primary medicament, wherein the primary dose setting mechanism and the secondary dose setting mechanism are configured to be set individually.

6. The drug delivery device according to claim 1, comprising a biasing member configured to urge the actuator in a proximal direction with respect to the housing.

7. The drug delivery device according to claim 1, wherein the actuation collar is configured such that the actuating movement of the actuation collar causes engagement with a secondary dose dispensing mechanism to activate the secondary dose dispensing mechanism.

8. The drug delivery device according to claim 1, wherein the first engagement section and the second engagement section are configured for meshed engagement.

9. The drug delivery device according to claim 1, wherein the first engagement section and the second engagement section are configured to disengage when the actuator is moved in a direction relative to the actuation collar opposite to the actuation movement.

10. The drug delivery device according to claim 1, wherein the first engagement section is provided with a first cam feature and the second engagement section is provided with a second cam feature, and
wherein the first cam feature and the second cam feature are configured to cause disengagement of the first engagement section and the second engagement section when the first cam feature and the second cam feature are moved against each other.

11. The drug delivery device according to claim 1, wherein the actuator has a pressing face configured to engage a pressure receiving section of the primary dose dispensing mechanism and arranged such that the actuation movement of the actuator closes a gap between the pressing face and the pressure receiving section so that the actuation movement is transferred to the pressure receiving section.

12. The drug delivery device according to claim 1, wherein the first engagement section is connected to a first latching portion and the second engagement section is connected to a second latching portion, and
wherein the first latching portion and the second latching portion are configured to be driven out of engagement with a force which corresponds to a force provided by the biasing member of the secondary drug delivery assembly during the resetting movement.

13. The drug delivery device according to claim 1 further comprising a locking element configured to rigidly engage the primary drug delivery assembly and the secondary drug delivery assembly and to be detachably received within the housing, wherein the housing comprises at least two housing parts configured to rigidly receive the locking element when the housing parts are assembled.

14. The drug delivery device according to claim 1 further comprising a locking element configured to rigidly engage the drug delivery assembly or the secondary drug delivery assembly and to be detachably received within the housing, wherein the housing comprises at least two housing parts configured to rigidly receive the locking element when the housing parts are assembled.

15. The drug delivery device according to claim 1 comprising at least one cartridge comprising a medicament.

16. The drug delivery device according to claim 15, wherein the medicament comprises a pharmaceutically active compound.

17. A drug delivery device comprising:
a housing retaining a primary drug delivery assembly a secondary drug delivery assembly, the primary drug delivery assembly configured to receive a primary reservoir containing a primary medicament, and the secondary drug delivery assembly configured to receive a secondary reservoir containing a secondary medicament, and
a dispense interface,
wherein the primary drug delivery assembly comprises a primary dose setting mechanism for setting a dose of the primary medicament,
wherein the secondary drug delivery assembly comprises a secondary dose setting mechanism for setting a dose of the secondary medicament,
wherein the secondary dose setting mechanism comprises a biasing member adapted to reset the secondary dose setting mechanism in a resetting movement and a trigger button for releasing the biasing member, wherein the trigger button is movable from a first trigger button position into a second trigger button position; and
a setting element movable between a first setting element position and a second setting element position, wherein the setting element is connected to the secondary dose setting mechanism, wherein during the resetting movement of the secondary dose setting mechanism, the setting element is moved from the second setting element position into the first setting element position; and
an actuator movable relative to the housing, wherein the actuator engages a primary dose dispensing mechanism of the primary drug delivery assembly during an actuation movement to dispense a set dose of the primary medicament through the dispense interface, wherein the actuator comprises a first engagement section configured to engage a second engagement section provided by an actuation collar such that the actuation movement of the actuator is transferred to the actuation collar,
wherein the actuation collar is moveable relative to the actuator between a first actuation collar position and a second actuation collar position, wherein in the second actuation collar position the first engagement section and the second engagement section are engaged, the actuation movement of the actuator is transferred to the actuation collar, the actuation collar engages the trigger button, and the trigger button moves into the second trigger button position,
wherein when the trigger button moves towards the second trigger button position, the trigger button releases the biasing member, wherein the biasing member is connected to the setting element such that the biasing member moves the setting element from the second setting element position into the first setting element position when the biasing member relaxes, and wherein the setting element is configured to drive the actuation collar out of engagement with the actuator when moving from the second setting element position into the first setting element position.

18. The drug delivery device according to claim 17, wherein the secondary drug delivery assembly comprises a secondary dose dispensing mechanism, wherein the secondary dose dispensing mechanism is actuated when the trigger button is moved from the first trigger button position into the second trigger button position to dispense a dose of the secondary medicament.

19. The drug delivery device according to claim 17, wherein the biasing member is adapted to drive a drive member in an axial direction when the biasing member is released, and wherein displacement of the drive member forces a bung in the secondary reservoir in a distal direction such that the secondary medicament in the secondary reservoir is driven out of the secondary reservoir.

20. The drug delivery device according to claim 17, wherein the biasing member is connected to the setting element such that the biasing member is prestressed when the setting element is moved from the first setting element position into the second setting element position.

* * * * *